(12) United States Patent
Mao et al.

(10) Patent No.: US 8,691,968 B2
(45) Date of Patent: Apr. 8, 2014

(54) COMPOSITIONS AND METHODS FOR THE PROTECTION OF NUCLEOPHILIC GROUPS

(75) Inventors: Fei Mao, Fremont, CA (US); Xing Xin, Foster City, CA (US); Wai-Yee Leung, San Ramon, CA (US)

(73) Assignee: Allelogic Biosciences Corporation, Hayward, CA (US)

( * ) Notice: Subject to any disclaimer, the term of this patent is extended or adjusted under 35 U.S.C. 154(b) by 296 days.

(21) Appl. No.: 13/001,735

(22) PCT Filed: Jul. 2, 2009

(86) PCT No.: PCT/US2009/003942
§ 371 (c)(1),
(2), (4) Date: Mar. 24, 2011

(87) PCT Pub. No.: WO2010/002476
PCT Pub. Date: Jan. 7, 2010

(65) Prior Publication Data
US 2011/0201010 A1     Aug. 18, 2011

Related U.S. Application Data

(60) Provisional application No. 61/078,327, filed on Jul. 3, 2008.

(51) Int. Cl.
*C07H 21/00* (2006.01)
*C12Q 1/68* (2006.01)
*B01L 3/00* (2006.01)

(52) U.S. Cl.
USPC ......... 536/25.3; 536/25.31; 435/6.1; 422/430

(58) Field of Classification Search
USPC ................. 536/25.3, 25.31; 435/6.1; 422/430
See application file for complete search history.

(56) References Cited

U.S. PATENT DOCUMENTS

| | | | |
|---|---|---|---|
| 3,218,288 A | 11/1965 | Waburton | |
| 4,362,818 A | 12/1982 | Cornelius et al. | |
| 5,565,339 A | 10/1996 | Bloch et al. | |
| 5,677,152 A | 10/1997 | Birch et al. | |

FOREIGN PATENT DOCUMENTS

| | | |
|---|---|---|
| EP | 0771870 A1 | 5/1997 |
| EP | 1078984 A1 | 2/2001 |
| WO | WO 1995/30647 | 11/1995 |
| WO | WO 2007/115702 A2 | 10/2007 |
| WO | WO 2007/115702 A3 | 11/2007 |

OTHER PUBLICATIONS

European search report and opinion dated Jul. 9, 2012 for EP Application No. 09773928.8.
International search report dated Nov. 10, 2009 for PCT Application No. US09-03942.

*Primary Examiner* — Jezia Riley
(74) *Attorney, Agent, or Firm* — Wilson Sonsini Goodrich & Rosati

(57) ABSTRACT

The present invention provides compositions, methods, and kits relating to the protection and deprotection of molecules comprising nucleophilic groups, such as the protection and deprotection of thermostable polymerases. Also provided are methods of performing nucleic acid amplification using polymerases protected according to the invention.

5 Claims, 10 Drawing Sheets

Scheme A

Scheme B

FIG. 7

Ct value of PCR using modified Taq

| Enzyme concentration | Modifying reagent | | |
|---|---|---|---|
| | None | Compound No. 3 | Compound No. 9 |
| 50 nM | 15.1 | 15.1 | 15.2 |
| 25 nM | 15.5 | 15.1 | 15.0 |
| 10 nM | 15.3 | 15.5 | 15.1 |
| 5 nM | 15.5 | 15.1 | 15.2 |
| 2.5 nM | 17.7 | 18.0 | 17.5 |

COMPOSITIONS AND METHODS FOR THE PROTECTION OF NUCLEOPHILIC GROUPS

BACKGROUND

The advent of Polymerase Chain Reaction (PCR) since the mid 1980s has revolutionized molecular biology through vastly extending the capability to identify, manipulate, and reproduce DNA. Nowadays PCR is routinely practiced in the course of conducting scientific researches, clinical diagnostics, forensic identifications, and environmental studies. Polymerase chain reaction (PCR) is a template-directed polymerization reaction that provides a method for amplifying specific nucleic acids in vitro. PCR can produce a million to a billion fold copies of a DNA template in a single enzymatic reaction within a matter of minutes to hours, enabling researchers to determine the size and sequence of a target DNA.

SEQUENCE LISTING

The instant application contains a Sequence Listing which has been submitted in ASCII format via EFS-Web and is hereby incorporated by reference in its entirety. Said ASCII copy, created on Mar. 13, 2011, is named 35754-705.831Seqlist.txt and is 3 Kilobytes in size.

Despite significant amount of progress made in the field of molecular biology and engineering, PCR remains a challenging application. One particular challenge is non-specific DNA amplification due to mis-priming, where the set of PCR primers hybridize to non-target DNA sequences. In principle, specific hybridization of a primer to the target DNA should ensure amplification of the target DNA and not other contaminating sequences. Specific priming can mostly be achieved at higher temperatures, such as at about 60° C.-70° C. These are also the temperatures at which the DNA polymerase Taq is most active. Thus, the chain extension reaction is typically set to take place at these temperatures to maximize specific DNA amplification. However, at a lower temperature, such as at room temperature, where components of PCR reactions are assembled, mis-priming occurs more frequently. Mis-priming may result from partial hybridization between the forward and reverse primers (i.e., primer-dimer formation), or from hybridization between a primer and a partially complementary sequence in the DNA template. These weakly formed hybrids may be sufficiently stable at or around room temperature. Because Taq still exhibits significant, though not optimal, activity at room temperature, the nonspecific hybrids can lead to nonspecific PCR products, which act as templates for even greater amount of nonspecific product formation during PCR reaction. In some cases, such as in the case of low template copy number, nonspecifically amplified products can be the dominant PCR products.

To overcome the aforementioned problem, various so-called "hot-start" PCR methods have been developed to suppress non-specific amplification at a temperature below the usual operating PCR temperatures. In general, most of the known hot-start methods employ a hot-start polymerase or polymerase complex that has no or very low activity at a temperature below the usual operating PCR temperatures. For example, polymerase-specific monoclonal antibodies have been developed to inhibit the enzyme activity by forming a polymerase-antibody enzyme complex. At room temperature, the enzyme complex is stable and thus inactive. When the temperature is raised to above 90° C., the enzyme complex releases the antibodies and thus becomes activated (U.S. Pat. No. 5,338,671, Scalice E R et al, Kellogg et al, (1994) Biotechniques 16:1134-1137). To sufficiently suppress the enzyme activity at room temperature, a high an antibody to enzyme molar ratio (typically 1 to 7 folds) is often required. The high antibody to enzyme ratio makes this method relatively costly. Another drawback is that the enzyme-antibody binding is reversible to some degree. Thus, even though the enzyme activity is significantly higher at the operating PCR temperatures, the enzyme may not be fully activated, compared to the enzyme without the presence of the antibodies.

Another approach to develop a hot-start polymerase is to chemically modify the lysine residues of the enzyme using a heat-sensitive modifying group. The modified enzyme is inactive at below the PCR temperature. However, once the modified enzyme is heated to a higher temperature, such as at above 90° C., the modifying group is released from the enzyme, thereby activating the enzyme (U.S. Pat. Nos. 5,677,152 and 6,183,998). This method has two attractive features. The first one is that both the modifying chemical and the manufacturing process for the modified enzyme are simple and inexpensive. The second feature is that the enzyme activation is, in principle, an irreversible process. Therefore, potentially a greater amount of enzyme activity can be achieved on activation, compared to the antibody-based hot-start enzyme. In practice, however, the conventional hot-start DNA polymerases that are chemically modified suffer from a number of profound drawbacks. Chemically modified hot-start enzymes are slow to start. For example, AmpliTaq Gold, a commercially available chemically-modified Taq, may require an activation time of as long as 15-20 minutes, which makes up a significant portion of the overall PCR time. Chemically modified Taq is also known to degrade significantly during storage as often indicated by progressively lower recovery activation efficiency. Moreover, following heat activation, chemically modified Taq in general does not recover the full enzyme capacity of the corresponding unmodified enzyme, even if the modified enzyme is freshly prepared.

SUMMARY OF THE INVENTION

There exists a considerable a need for modified enzymes (e.g., polymerases) to improve performance of PCR and other chemical reactions. Specifically, there is a need for polymerases that are substantially inactive in the conditions in which the PCR reaction is assembled, but can be activated quickly and with high efficiency once activation of the reaction is desired. Additionally, polymerases for this and other applications should be stable during storage and should be relatively inexpensive to manufacture. The present invention addresses one or more of these needs and provided related advantages as well.

In one embodiment, the present invention provides a method of reversibly protecting a nucleophilic group comprising: a) providing a nucleophilic group; b) reacting the nucleophilic group with a reagent of the formula:

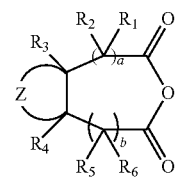

wherein $R_1$, $R_2$, $R_5$ and $R_6$ are hydrocarbon residues, substituted or unsubstituted;

a and b are independently 0 or 1;

$R_3$ and $R_4$ are independently —H or a substituent, wherein at least one of $R_3$ and $R_4$ is a substituent when a and b are 0, and wherein $R_3$ and $R_4$ are cis;

Z forms a 3, 4, 5, 6, 7 or 8-membered ring.

In some embodiments, a and b are 0. In related embodiments, $R_3$ or $R_4$ is a substituent. For example, $R_3$ or $R_4$ is an alkyl group such as methyl. In some embodiments, Z forms a 6-membered ring. Alternatively, Z forms a bicyclic moiety. In particular embodiments, the reagent has the formula:

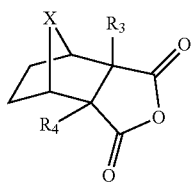

wherein X is O or alkylene, substituted or unsubstituted.

In some embodiments, the nucleophilic group is an ϵ-amino group of a lysine residue of a polypeptide. In other embodiments, the polypeptide is a polymerase.

The invention also provides a method of reversibly protecting a nucleophilic group comprising: a) providing a nucleophilic group; b) reacting the nucleophilic group with a reagent of the formula:

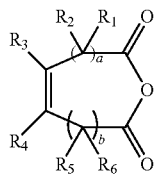

wherein $R_1$, $R_2$, $R_5$ and $R_6$ are hydrocarbon residues, substituted or unsubstituted;

a and b are independently 0 or 1 and at least one of a and b is 1;

$R_3$ and $R_4$ are independently —H or a substituent, wherein $R_3$ and $R_4$ optionally form a ring and further wherein $R_3$ and $R_4$ are cis.

In some embodiments, a is 1 and b is 0. Alternatively, a is 0 and b is 1. $R_3$ or $R_4$ may be a substituent. For example, $R_3$ or $R_4$ may be an alkyl group such as methyl. In other embodiments, $R_3$ and $R_4$ form a 6-membered ring and/or an aromatic ring. In specific embodiments, $R_3$ and $R_4$ form a phenyl ring which is substituted with up to four additional substituents.

In particular embodiments of the method, the reagent has the formula:

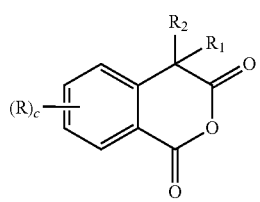

wherein R is a monovalent substituent and c is 0, 1, 2, 3 or 4.

In another aspect, the invention provides methods for preparing a protected lysine residue in a polypeptide comprising reacting a six-membered or seven-membered cyclic anhydride with an ϵ-amino group of a lysine residue, wherein the reaction results in a protected lysine residue comprising an amide and a carboxylic acid; and further wherein the carboxylic acid is conformationally constrained with respect to the amide such that the carboxylic acid exhibits a greater propensity to react with the amide relative to a corresponding protected lysine residue comprising an unconstrained carboxylic acid.

Deprotection of the protected lysine residue of the polypeptide may occur more readily relative to the corresponding protected lysine residue comprising the unconstrained carboxylic acid. For example, the carboxylic acid may be conformationally constrained with respect to the amide by the presence of a 5, 6 or 7-membered ring. The carboxylic acid may also be conformationally constrained with respect to the amide by alkyl group substitution. For example, a position of alkyl group substitution may be adjacent to the amide. Alternatively, a position of alkyl group substitution may be adjacent to the carboxylic acid.

The invention also provides a method for preparing a protected lysine residue in a polypeptide comprising reacting a five-membered cyclic anhydride with an ϵ-amino group of a lysine residue, wherein the reaction results in a protected lysine residue comprising an amide and a carboxylic acid; and further wherein the carboxylic acid is conformationally constrained with respect to the amide by a substituted 3, 4, 5, 6 or 7-membered ring such that the carboxylic acid exhibits a greater propensity to react with the amide relative to a corresponding protected lysine residue comprising an unconstrained carboxylic acid.

The 3, 4, 5, 6 or 7-membered ring may be substituted with an alkyl group further conformationally constraining the carboxylic acid with respect to the amide. For example, a position of alkyl group substitution may be adjacent to the amide. Alternatively, a position of alkyl group substitution may be adjacent to the carboxylic acid.

The present invention additionally provides a method of amplifying a template nucleic acid comprising: a) providing an amplification reaction mixture comprising a population of polymerases that is reversibly protected such that the population of polymerases is convertible to a corresponding population of unprotected polymerases with a yield of at least 80% when subjected to a suitable deprotection condition for less than about 10 minutes; b) deprotecting individual polymerases in the population of protected polymerases to corresponding unprotected polymerases; and c) subjecting said mixture under suitable amplification conditions such that the template is amplified.

In one embodiment, the converting step comprises incubating the population of protected polymerases for less than 10 minutes under said suitable deprotection condition such that more than 80% of the population of protected polymerases is converted to unprotected polymerases.

In another aspect, a method of amplifying a template nucleic acid is provided comprising: a) providing an amplification reaction mixture comprising a polymerase which is reversibly protected such that it is convertible to a corresponding unprotected polymerase with a certainty of at least 80% when subjected to a suitable deprotection condition for less than about 10 minutes; b) deprotecting the protected polymerase to said unprotected polymerase; and c) subjecting said amplification reaction mixture under conditions such that the template is amplified. Alternatively, a method of amplifying a template nucleic acid is provided comprising: a) providing an amplification reaction mixture comprising a population of polymerases that is reversibly protected such that the population of polymerases is convertible to a corresponding population of unprotected polymerases with a yield of at least 50% when subjected to a suitable deprotection condition for less than about 15 minutes; b) deprotecting individual polymerases in the population of protected polymerases to corresponding unprotected polymerases; c) subjecting said mixture under suitable amplification conditions such that the template is amplified. Said deprotection may take place, for example, under a pH between about 6 and 11. In other embodiments, said deprotection may take place under a temperature greater than about 85° C. Alternatively, said deprotection may take place under a temperature between about 90° C. and 100° C., or between about 55 and 65° C. The unprotected polymerases may be Taq polymerases.

In some embodiments, the polymerase is protected by reacting with a reagent as indicated above. In other embodiments, the reaction mixture comprises one or more amplification reagents selected from the group consisting of a primer, a nucleotide, a template and a nucleic acid detecting agent. Alternatively, the amplification reaction is performed on a substrate.

The present invention further provides a composition comprising a population of protected polymerases, wherein a) the population of protected polymerases is substantially inactive compared to a corresponding population of unprotected polymerases; b) individual polymerases within said population of protected polymerases are convertible to corresponding unprotected polymerases with a yield of at least 80% as measured by an increase in polymerase activity, when subjected to suitable deprotection conditions for less than 10 minutes. The polymerase activity may be measured as the ability to perform template-dependent extension of a nucleic acid primer. For example, the polymerase activity may be evaluated in a nucleic acid amplification reaction. Said deprotection may take place, for example, under a pH between about 6 and 11. In other embodiments, said deprotection may take place under a temperature greater than about 85° C. Alternatively, said deprotection may take place under a temperature between about 90° C. and 100° C. Also encompassed by the present invention is an amplification reaction mixture comprising a population of protected polymerases according to the invention and one or more amplification reagents selected from the group consisting of a nucleotide, a template nucleic acid and a primer. The amplification reaction mixture may additionally comprise a nucleic acid detection agent that provides a detectable signal indicative of the presence of an amplified template nucleic acid.

In another aspect, a composition is provided comprising: a) a first population of protected polymerases, wherein the first population is substantially inactive relative to a corresponding first population of unprotected polymerases; b) a second population of protected polymerases, wherein the second population is substantially inactive relative to a corresponding second population of unprotected polymerases; wherein individual polymerases within said first population of protected polymerases are convertible to corresponding unprotected polymerases under a first set of suitable deprotection conditions, but under which conditions individual polymerases of said second population of protected polymerases are not convertible to corresponding unprotected polymerases; and further wherein individual polymerases within said second population of protected polymerases are convertible to corresponding unprotected polymerases under a second set of suitable deprotection conditions.

The first population of protected polymerases may comprise RNA polymerases. In another embodiment, the second population of protected polymerases comprises thermostable DNA polymerases. Together, the first and second populations of polymerase may carry out a reverse transcription-coupled PCR reaction. For example, deprotection under the first set of deprotection conditions may take place under a temperature of about 40° C. to about 60° C. Deprotection under the second set of suitable deprotection conditions may take place under a temperature of about 80° C. to about 100° C.

The invention also provides a kit comprising a protected polymerase according to the invention and a nucleic acid detection reagent. The nucleic acid detection reagent may be a fluorescent reagent such as for example EvaGreen or SYBR Green I. A kit may additionally comprises one or more reagents selected from the group consisting of a primer, template, nucleoside phosphate and buffer. A kit may additionally comprise a user instruction manual. Such a user manual may instruct a user to perform a reaction such as a nucleic acid amplification reaction.

Also provided herein is an instrument for use in a nucleic acid amplification reaction comprising multiple thermal cycles, comprising: an automated thermal cycler capable of alternately heating and cooling, and adapted to receive, at least one reaction vessel containing an amplification reaction mixture comprising a template nucleic acid, a nucleotide, a nucleic acid detecting agent, and a population of protected polymerases of the invention; wherein the cycler is programmable to control initiation of the amplification reaction by controlling deprotection of the protected polymerases. In some embodiments, the instrument additionally comprises a display capable of indicating the extent of deprotection of the protected polymerases and/or indicate the set of conditions in which one or more populations of deprotected polymerases may become deactivated. Such a display may aid the user of the instrument in performing the reactions disclosed herein.

The instrument may further comprise a detector operable to detect a fluorescence optical signal while the amplification reaction is in progress, which fluorescence optical signal is related to the presence and/or amount of amplified nucleic acid in the reaction vessel. The detector is for example operable to detect a fluorescence optical signal in at least one of the following wavelength regions: from about 510 to about 530 nm, from about 540 to about 550 nm, from about 560 to about 580 nm, from about 585 to about 595 nm, from 590 to about 610 nm, from 660 to about 680 nm, from about 690 to about 710 nm, or from 770 to about 790 nm. The instrument may also be adapted to receive a plurality of reaction vessels, each containing an amplification reaction mixture.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7. Ct values of DNA amplifications using unprotected Taq polymerase and Taq polymerases protected with compound No. 1 and compound No. 9, respectively.

DETAILED DESCRIPTION OF THE INVENTION

Figure 1:
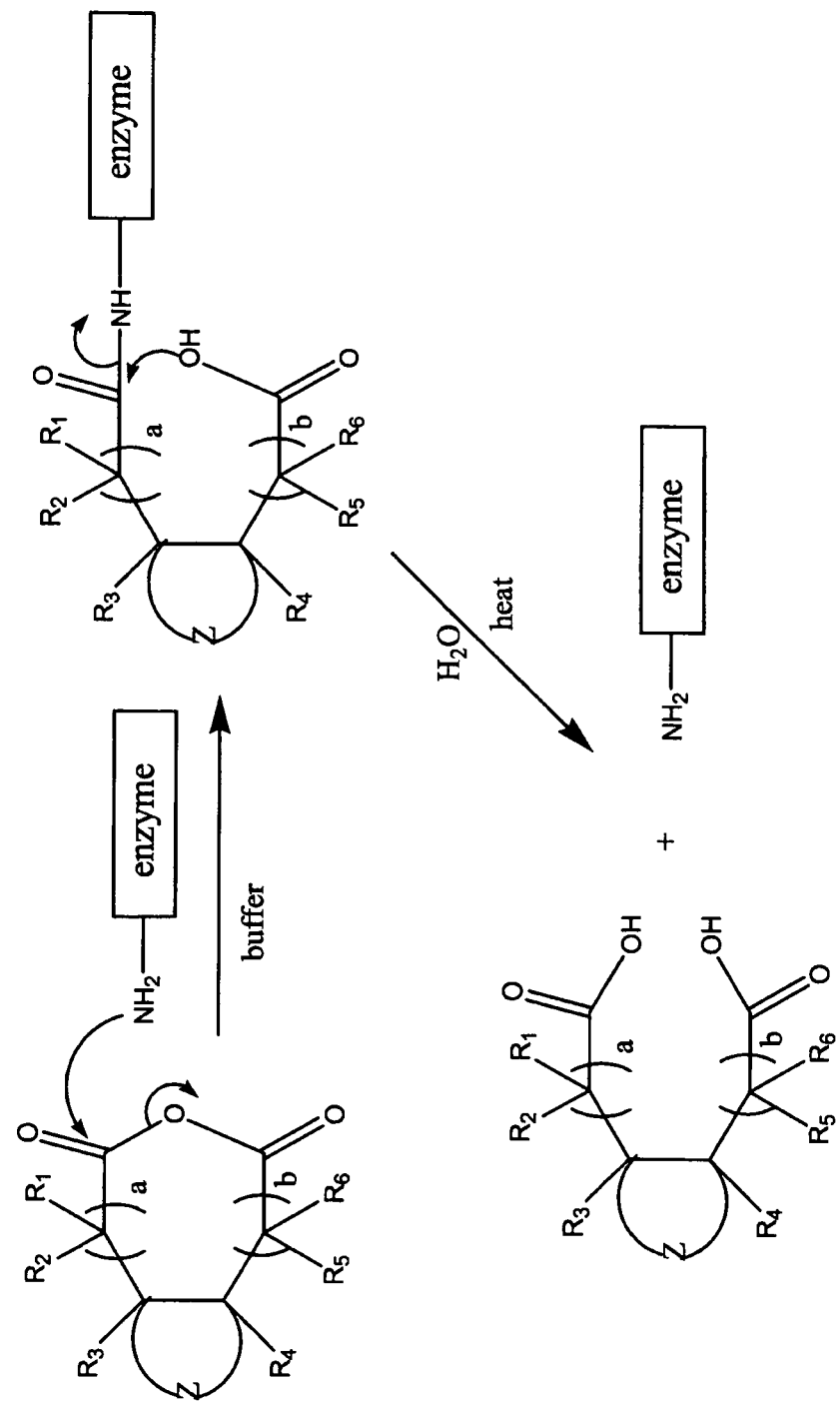
FIGS. 1 and 2. Amine protection and deprotection using protecting reagents of the invention.

The present invention provides compositions and methods for the protection and deprotection of nucleophilic groups in various organic molecules, including biologically significant molecules such as polypeptides.

DEFINITIONS

The term "nucleophilic group" is used herein to refer to any moiety capable of reacting with a corresponding electrophilic group under suitable reaction conditions. Nucleophilic groups include, but are not limited to, organic nucleophilic groups such as amine, thiol and hydroxl moieties. Nucleophilic groups may be attached to organic molecules of any size or to any other structure or support, such as a surface.

As used herein, "nucleic acid amplification" refers to an enzymatic reaction in which the target nucleic acid is increased in copy number. Such increase may occur in a linear or in an exponential manner.

The term "polypeptide" encompasses two or more naturally or non-naturally-occurring amino acids joined by a covalent bond such as an amide bond. Polypeptides as described herein include full length proteins as well as shorter amino acid sequences (e.g., fragments of naturally-occurring proteins or synthetic polypeptide fragments).

The term "polymerase" as used herein means any molecule or molecular assembly that can polymerize a set of monomers into a polymer having a predetermined sequence of the monomers, including, without limitation, naturally occurring polymerases or reverse transcriptases, mutated naturally occurring polymerases or reverse transcriptases, where the mutation involves the replacement of one or more or many amino acids with other amino acids, the insertion or deletion of one or more or many amino acids from the polymerases or reverse transcriptases, or the conjugation of parts of one or more polymerases or reverse transcriptases, non-naturally occurring polymerases or reverse transcriptases. The term polymerase also embraces synthetic molecules or molecular assemblies that can polymerize a polymer having a pre-determined sequence of monomers, or any other molecule or molecular assembly that may have additional sequences that facilitate purification and/or immobilization and/or molecular interaction of the tags, and that can polymerize a polymer having a pre-determined or specified or templated sequence of monomers.

As used herein, the term "thermostable enzyme" refers to an enzyme which is capable of catalyzing or facilitating a chemical reaction at a temperature higher than about 40° C.

As used herein, the term "conformationally constrained" means that at least one of a rotational or translational degree of freedom in a molecule or moiety is reduced or eliminated. Consequently, conformationally constrained molecules may be substantially locked in a particular conformation, or may have one or more substituents substantially confined to a particular conformation and/or position with respect to the remainder of the molecule.

The terms "protection" and "protected" are used herein to refer to the state of a molecule after it has been reacted with a protecting reagents of the invention. The terms "deprotection" or "deprotected" similarly refer to the state of the molecule after suitable deprotection conditions have been induced. When the molecule to be protected and/or deprotected comprises multiple nucleophilic groups capable of reacting with the protecting reagents of the invention, it is to be understood that it is not necessary for each and every nucleophilic group to be deprotected in order for the molecule to be considered "deprotected", and that a molecule is considered to be in a "protected" or "deprotected" state based on its functional characteristics. By way of example only, if a polymerase comprising several nucleophilic groups such as the ε-amino group of lysines, the polymerase is considered protected if, after reacting with a protecting reagent of the invention, the polymerase is rendered inactive. Similarly, the polymerase is considered deprotected if, after induction of suitable deprotection conditions, the activity of the polymerase is restored, regardless of whether each and every lysine group in the polymerase is itself deprotected.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl.

"Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to a $C_1$-$C_5$ alkyl group, as defined above, wherein one of the $C_1$-$C_5$ alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—C(O)—CH$_3$, —CH$_2$—CH$_2$—NH—C(O)—CH$_3$—CH$_3$, and —CH$_2$—CH$_2$—NH—C(O)—CH=CH$_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, 3 to 8 carbons, or 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "hydrocarbon residue" refers to any alkyl, cycloalkyl, alkenyl, cycloalkenyl, and alkynyl group.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

Modifying Reagents of the Invention

Figure 2:
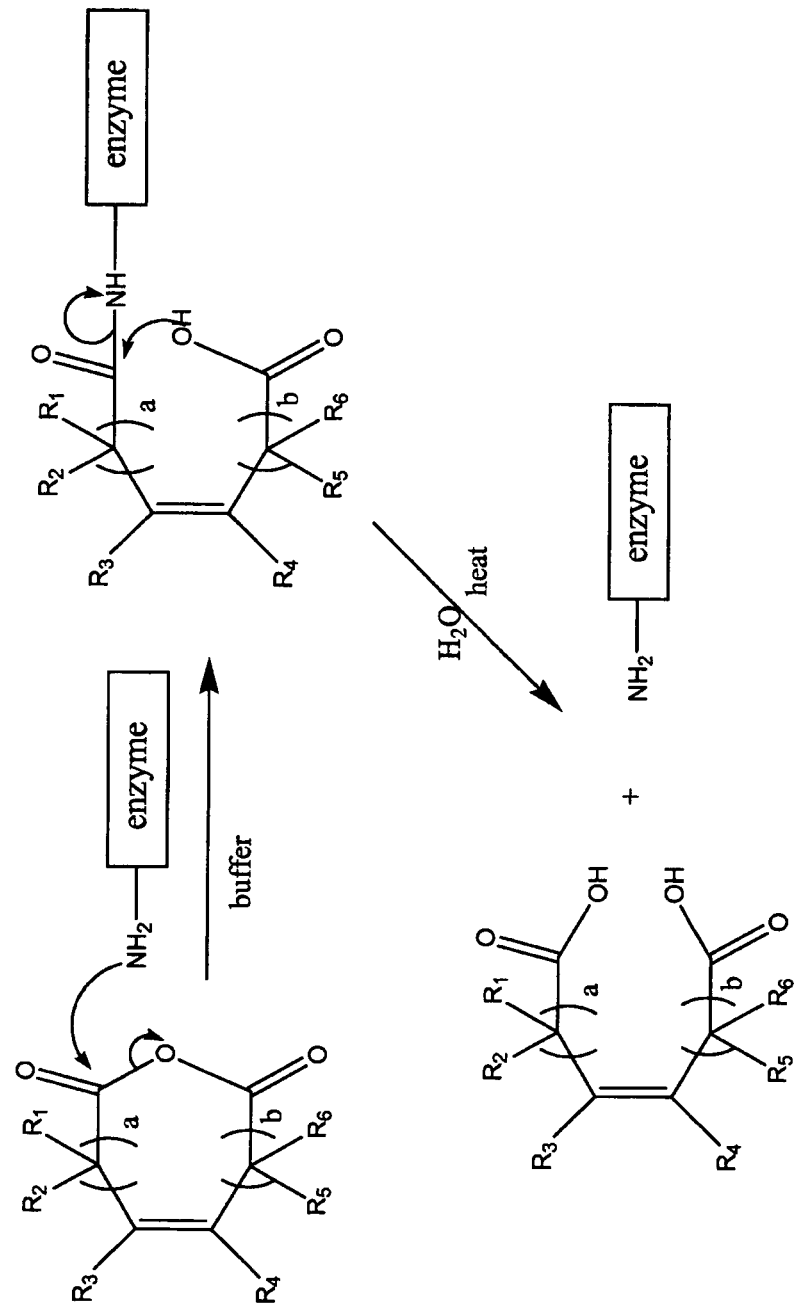

In one aspect, the present invention provides protecting reagents capable of reacting with nucleophilic groups wherein the reaction results in the protection of said nucleophilic groups. For example, a protecting reagent may reacts with the ε-amino group of lysine residues or the N-terminal amino group of a polypeptide (e.g., an enzyme) to form an amide linkage and a free carboxylate group (FIGS. 1 and 2). Among the lysine residues in the enzyme, at least one may be generally contributing to maintaining protein conformation and/or enzyme function. When such a lysine residue becomes protected, the enzyme may become inactivated.

Because the amide bond between the modifying group and each lysine amine group is sufficiently stable at a lower temperature, such as at or below room temperature, a protected enzyme according to the invention remains inactivated during storage, shipping, handling and component assembling for reactions involving the enzyme. However, at a higher temperature, the free carboxylate group near the amide bond acts as a strong nucleophile that cyclizes to form back the anhydride protecting reagent and at the same time frees up the amino group. Because the reaction takes place in a buffer, the resulting protecting reagent quickly hydrolyzes into a dicarboxylate compound (FIGS. 1 and 2), thus leading to irreversible de-modification of the amino group.

In one aspect, the present invention provides a reagent of the formula I:

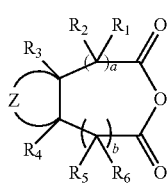

(Formula I)

wherein $R_1$, $R_2$, $R_5$ and $R_6$ are hydrocarbon residues, substituted or unsubstituted;

a and b are independently 0 or 1; $R_3$ and $R_4$ are independently —H or a substituent, wherein at least one of $R_3$ and $R_4$ is a substituent when a and b are 0, and wherein $R_3$ and $R_4$ are cis; and Z forms a 3, 4, 5, 6, 7 or 8-membered ring.

In some embodiments of the invention, a and b are both 0. Alternatively, at least one of a and b is 1. In other embodiments, $R_3$ or $R_1$ is a substituent. For example, $R_3$ or $R_4$ is an alkyl substituent such as a methyl or ethyl group. In a specific embodiment, a and b are 0 and $R_3$ and $R_4$ are substituents. The moiety Z forms a 6-membered ring in certain embodiments. In other cases, Z forms a bicyclic moiety which may be aromatic, nonaromatic or may comprise an aromatic and a nonaromatic ring.

In some embodiments, the reagent has the formula:

wherein X is O or alkylene, substituted or unsubstituted. For example, X may be —CH$_2$—, —CH$_2$—CH$_2$— or the like.

The protecting reagent may possess a more conformationally constrained structure such that two carbonyl groups of the cyclic anhydride are favored to be in proximity even after the anhydride ring is opened following the reaction with a nucleophile. The conformational constraint is achieved in part by the presence of the ring Z and may be further enhanced if at least one of $R_3$ and $R_4$ is a substituent. When the anhydride ring is a 6- or 7-membered ring, the presence of $CR_1R_2$ or $CR_5R_6$ or both $CR_1R_2$ and $CR_5R_6$ is necessary to further ensure conformational constraints.

In another aspect, the invention provides a reagent of the formula II:

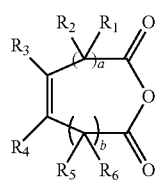

(Formula II)

wherein $R_1$, $R_2$, $R_5$ and $R_6$ are hydrocarbon residues, substituted or unsubstituted;

a and b are independently 0 or 1 and at least one of a and b is 1;

$R_3$ and $R_4$ are independently —H or a substituent, wherein $R_3$ and $R_4$ optionally form a ring and further wherein $R_3$ and $R_4$ are cis.

In some embodiments, a is 1 and b is 0, or a is 0 and b is 1, or both a and b are 1. $R_3$ or $R_4$ may be a substituent such as a n alkyl group, for example methyl or ethyl. Alternatively, $R_3$ and $R_4$ form a 6-membered ring. Such a ring may be aromatic or nonaromatic. For example, $R_3$ and $R_4$ can form an aromatic 6-membered ring such as a phenyl ring which is substituted with up to four additional substituents.

In one embodiment, the reagent has the formula:

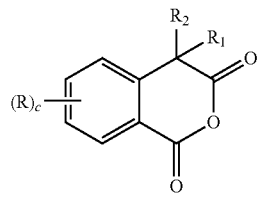

wherein R is a monovalent substituent and c is 0, 1, 2, 3 or 4.

The table below shows a list of exemplary protecting reagents according to the invention:

TABLE 1

Exemplary protecting reagents according to the invention

| Modifying reagent | Structure |
| --- | --- |
| Compound No. 1 | 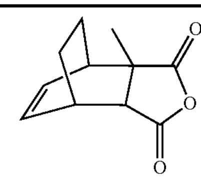 |
| Compound No. 2 | 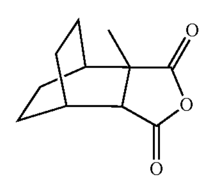 |
| Compound No. 3 | 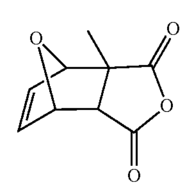 |

TABLE 1-continued

Exemplary protecting reagents according to the invention

| Modifying reagent | Structure |
|---|---|
| Compound No. 4 | (structure) |
| Compound No. 5 | (structure) |
| Compound No. 6 | (structure) |
| Compound No. 7 | (structure, with H₃CO substituent) |
| Compound No. 8 | (structure, with Cl substituent) |
| Compound No. 9 | (structure) |
| Compound No. 10 | (structure, with S) |

Methods of Preparing Reagents of the Invention

Figure 3:
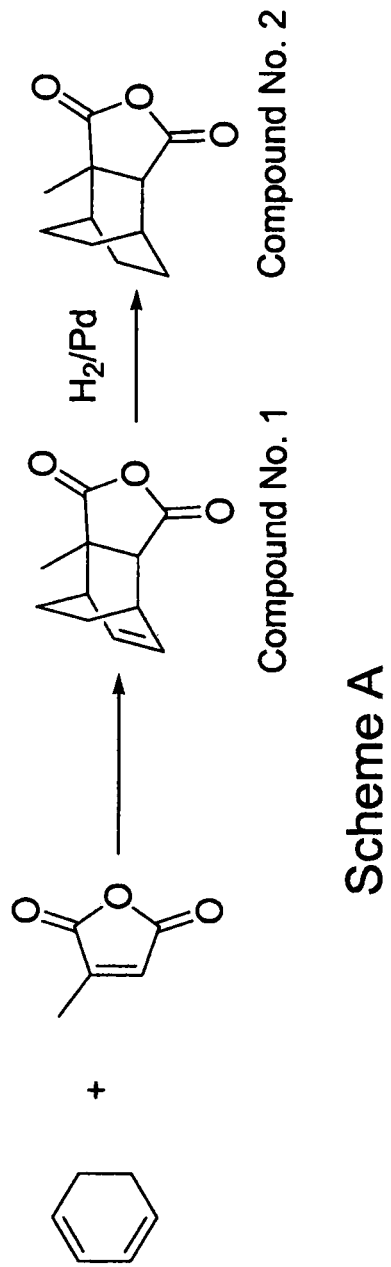
FIGS. 3 and 4. Syntheses of protecting reagents of the invention.
Figure 3:
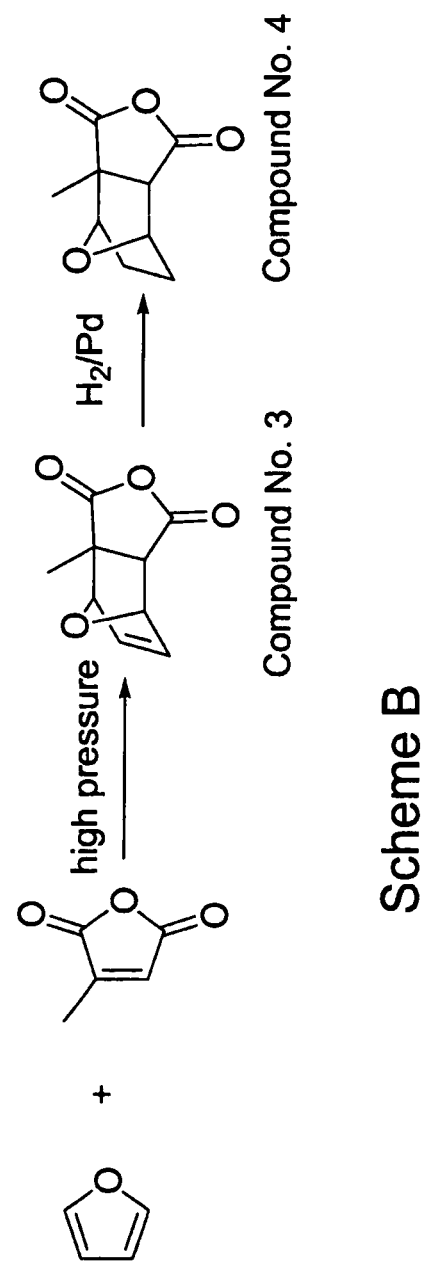
Figure 4:
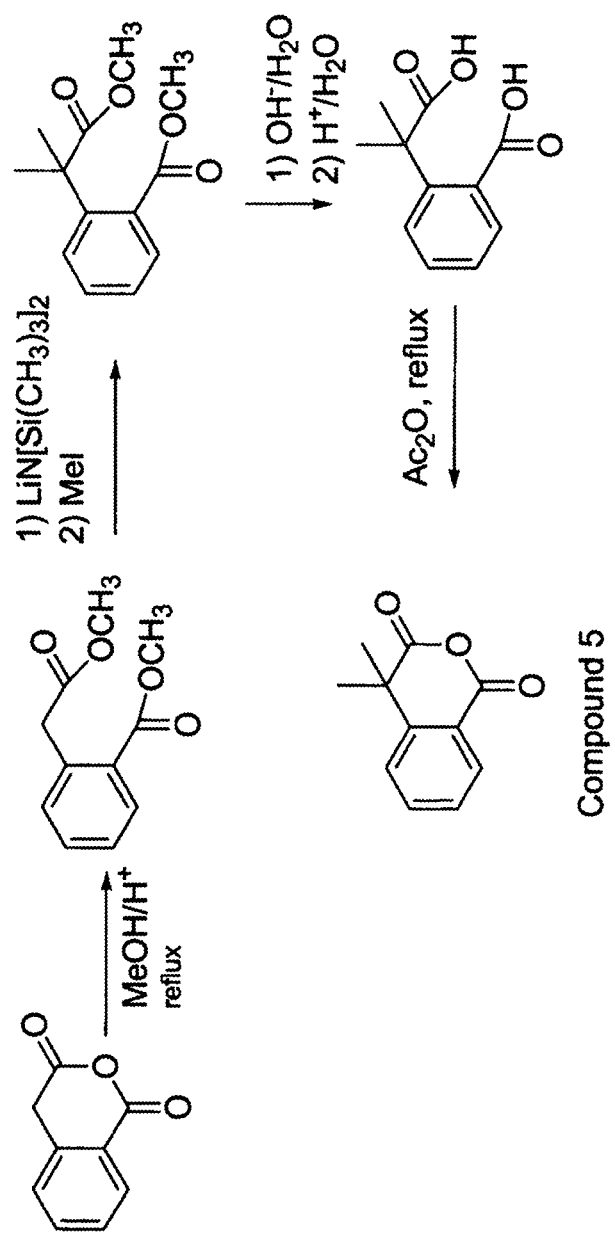

The protecting reagents of the invention can be readily synthesized according to the methods disclosed herein and others known in the art. For example, some of the protecting reagents according to formula II can be synthesized via Diels-Alder reactions from maleic anhydride or a suitable maleic anhydride derivative and a suitable diene. A resulting Diels-Alder product can either be used directly as a protecting reagent or be derivatized further to prepare a protecting reagent. As explained herein, generally a Diels-Alder product is derivatized further by hydrogenating the C=C double bond of the molecule to a saturated C—C single bond, thereby preventing the Diels-Alder product from reverting back to the maleic anhydride starting material, which may happen at higher temperatures. FIG. 3 shows the syntheses of four typical protecting reagents, compound No. 1, compound No. 2, compound No. 3 and compound No. 4, via Diels-Alder reactions. It is understood that Diels-Alder reactions may form an endo-isomer and an exo-isomer. Thus, each of compound Nos. 1-4 may represent a mixture of two isomers. In general, for the purpose of the invention, both the endo- and exo-isomers are suitable as protecting reagents. Also, certain Diels-Alder reactions may require high pressure to take place. These are usually reactions that form sterically hindered adducts. For example, the reaction between furan and citraconic anhydride only proceeds under high pressure (Scheme B of FIG. 3). High pressure Diels-Alder reactions have been described previously (Dauben, W. G.; Krabbenhoft, H. O. *J. Am. Chem. Soc.* 98, 1992 (1976)). Modifying reagents of formula 3 or 4 can also be prepared from readily available starting materials. FIG. 4 illustrates a typical method for preparing a protecting reagent of formula 4 (compound No. 5). The synthesis starts from the commercially available homophthalic anhydride by converting it to the dimethyl ester first, followed by dimethylation of the methylene carbon. The dimethyl ester intermediate is hydrolyzed to the free acid, which is then converted to the final cyclic anhydride protecting reagent. One skilled in the art will readily understand that the aromatic ring of compound No. 5 can be easily modified by various substitutents using known chemistries. Depending on whether substituents on such an aromatic ring are electron-donating or electron-withdrawing, they are expected to affect the reactivity of the carbonyl groups of the reagent, thus allowing fine-tuning of the reaction rate between the carboxylic acid and the amide group, and therefore would allow fine-tuning of the temperature at which the protected enzyme can be activated.

Methods of Preparing Protected Nucleophilic Groups

The use of the protecting reagents of the invention can be applied to the reversible modification or protection of enzymes, other proteins and any other nucleophilic groups, for example small amine-containing molecules. For example, they may be used in the temporary protection or masking of small amine-containing compounds during organic synthesis or biochemical manipulations.

In some embodiments, the nucleophile to be reacted with the protecting reagents of the invention are s-amino groups of lysine residues comprised in enzymes. The resulting protected enzymes may comprise one or more of its amino groups covalently attached with a modifying group. Typically, more than one amino group of the enzyme is protected due to the presence of multiple lysine residues in the protein sequence of the enzyme. Additionally, the N-terminal amine(s) groups of any enzyme or polypeptide may also react with the protecting reagents of the invention. When desired, the degree of enzyme inactivation may be adjusted by controlling the extent of enzyme modification, for example the number of amino groups protected. In general, the more amino groups are protected, the more the enzyme will be inactivated. When the number of amino groups protected reaches a threshold value, the enzyme is completely inactivated. This threshold value may be obtained empirically by modifying the enzyme with increasing amount of the protecting reagent and test the activity of the protected enzyme. Such a determination is within the capability of a person skilled in the art.

Polypeptide modification of the invention is carried out by incubating a polypeptide to be protected in the presence of a protecting reagent of the invention in an aqueous buffer. The amount of reagent required depends on the degree of modification desired. To completely or nearly completely inactivate a thermostable enzyme, the reagent/enzyme molar ratio typically needs to reach a threshold value, which is generally determined empirically. The range of reagent/protein molar ratio can be determined empirically for a given protein and protecting reagent under a given labeling condition using standard methods known in the art. The buffer is generally an alkaline buffer with pH from ~7.5 to about ~10, more preferably with pH from ~8 to ~9. Examples of suitable buffers include, but not limited to, bicarbonate buffer, borate buffer, phosphate buffer and Tris buffer. The buffer concentration is generally at or above about 50 mM, more preferably at or above 100 mM. The modification reaction can be carried out at a temperature from about 4° C. to about 40° C., more preferably at a temperature from about 4° C. to about 25° C. The incubation time is generally from about 15 min to overnight. The exact reaction time varies, depending on the reaction temperature and reagent/protein molar ratio. At a higher reaction temperature and higher reagent/protein ratio, for example, a shorter reaction time is needed. On the other hand, a lower reaction temperature and a lower reagent/protein ratio generally may require a longer reaction time. Upon completion of the reaction, the hydrolyzed protecting reagent is optionally removed from the protected protein using a method such as dialysis. One advantage of enzyme modification according to the invention may be that following the modification reaction removal of the hydrolyzed protecting reagent is generally not necessary because unremoved protecting reagents of the invention usually do not interfere with the storage and use of the protected enzymes.

Examples of suitable polymerases include, but are not limited to, enzymes for nucleic acid amplification reactions, enzymes for ligation reactions and enzymes with exo- and/or endonucleolytic activities. In certain embodiments, the polymerase is an RNA polymerase. In other embodiments, the polymerase is a DNA polymerase, such as DNA polymerase I, II, or III or DNA polymerase $\alpha$, $\beta$, or $\gamma$, terminal deoxynucleotidyl transferase (TdT) or telomerase. In other embodiments, suitable polymerases include, but are not limited to, a DNA dependent RNA polymerase, a primase, or an RNA dependant DNA polymerase (reverse transcriptase). For example, suitable polymerases include T7 DNA polymerase, Kornberg DNA polymerase I, Klenow DNA polymerase, Taq DNA polymerase, Micrococcal DNA polymerase, alpha DNA polymerase, AMV reverse transcriptase, M-MuLV reverse transcriptase, reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase, ribonucleotide incorporating DNA polymerase, and the like. The sequences of certain of these nucleotide incorporating biocatalysts are publicly available from various sources including, e.g., GenBank and the like.

In some embodiments, DNA polymerases that possess substantial 3' 5' exonuclease activity are used to perform the present invention. Such enzymes include the Pfu DNA polymerase, *E. coli* DNA polymerase I, Klenow fragment, T-4 polymerase, T-7 polymerase, *E. coli* DNA pol III, Ultima DNA Polymerase (Cetus), Vent DNA and Deep Vent DNA polymerases (New England Biolabs). When using the subject compositions in reaction mixtures that are exposed to elevated temperatures, e.g., during the PCR technique, thermostable DNA polymerases may be used. Examples of the thermostable DNA polymerases that possess substantial 3' 5' exonuclease activity include Vent DNA polymerase, Ultima DNA polymerase, Deep Vent DNA polymerase, and Pfu DNA polymerases. For example, a DNA polymerase possessing 3'-5' exonuclease activity for use in subject composition is the Pfu DNA polymerase which is commercially available from Stratagene (La Jolla, Calif.). and described in U.S. patent application Ser. No. 07/803,627 filed Dec. 2, 1991. Other thermostable enzymes are typically derived from an organism such as *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax, Bacillus stearothermophilus*, or the like.

DNA polymerases and their properties are described in detail in, among other places, DNA Replication 2nd edition, Kornberg and Baker, W.H. Freeman, New York, N.Y. (1991). DNA polymerases with less 3' 5' exonuclease activity for use in the subject compositions and methods may be isolated from natural sources or produced through recombinant DNA techniques. DNA polymerases with less 3' 5' exonuclease activity than the 3' 5' exonuclease activity of the enzyme with substantial 3' 5' exonuclease activity, i.e., 3' 5' single-stranded exonuclease activity, include Taq DNA polymerases and Sequenase™ (modified bacteriophage T7 DNA polymerase, available from U.S. Biochemical, Columbus, Ohio). Additionally, a person of average skill in the art will recognize that exonuclease deficient polymerases such as Exo-Pfu DNA polymerase, Vent® (exo-) DNA polymerase, Deep Vent® (exo-) DNA polymerase, and the like may be suitably used in the subject compositions. Taq DNA polymerase, Sequenase™, Exo-Pfu DNA polymerase, Vent (exo-) DNA polymerase, and Deep Vent (exo-) DNA polymerase are all examples of DNA polymerases that substantially lack 3' 5' exonuclease activity.

Details relating to useful polymerases and enzymes are also provided in, e.g., U.S. Pat. No. 5,939,292, entitled "THERMOSTABLE DNA POLYMERASES HAVING REDUCED DISCRIMINATION AGAINST RIBO-NTPS," which issued Aug. 17, 1999 to Gelfand et al., U.S. Pat. No. 4,889,818, entitled "PURIFIED THERMOSTABLE ENZYME," which issued Dec. 26, 1989 to Gelfand et al., U.S. Pat. No. 5,374,553, entitled "DNA ENCODING A THERMOSTABLE NUCLEIC ACID POLYMERASE ENZYME FROM *THERMOTOGA MARITIMA*," which issued Dec. 20, 1994 to Gelfand et al., U.S. Pat. No. 5,420,029, entitled "MUTATED THERMOSTABLE NUCLEIC ACID POLYMERASE ENZYME FROM *THERMOTOGA MARITIMA*," which issued May 30, 1995 to Gelfand et al., U.S. Pat. No. 5,455,170, entitled "MUTATED THERMOSTABLE NUCLEIC ACID POLYMERASE ENZYME FROM *THERMUS* SPECIES Z05," which issued Oct. 3, 1995 to Abramson et al., U.S. Pat. No. 5,466,591, entitled "5' TO 3' EXONUCLEASE MUTATIONS OF THERMOSTABLE DNA POLYMERASES," which issued Nov. 14, 1995 to Abramson et al., U.S. Pat. No. 5,618,711, entitled "RECOMBINANT EXPRESSION VECTORS AND PURIFICATION METHODS FOR *THERMUS THERMOPHILUS* DNA POLYMERASE," which issued Apr. 8, 1997 to Gelfand et al., U.S. Pat. No. 5,624,833, entitled "PURIFIED THERMOSTABLE NUCLEIC ACID POLYMERASE ENZYME FROM *THERMOTOGA MARITIMA*," which issued Apr. 29, 1997 to Gelfand et al., U.S. Pat. No. 5,674,738, entitled "DNA ENCODING THERMOSTABLE NUCLEIC ACID POLYMERASE ENZYME FROM *THERMUS* SPECIES Z05," which issued Oct. 7, 1997 to Abramson et al., U.S. Pat. No. 5,789,224, entitled "RECOMBINANT EXPRESSION VECTORS AND PURIFICATION METHODS FOR *THERMUS THERMOPHILUS* DNA POLYMERASE," which issued Aug. 4, 1998 to Gelfand et al., U.S. Pat. No. 5,795,762, entitled "5' TO 3' EXONUCLEASE MUTATIONS OF THERMOSTABLE DNA POLYMERASES," which issued Aug. 18, 1998 to Abramson et al., U.S. Pat. Application Publication No. US 2002/0012970, entitled "HIGH TEMPERATURE REVERSE TRANSCRIPTION USING MUTANT DNA POLYMERASES," which published Jan. 31, 2002 by Smith et al., and U.S. patent application Ser. No. 10/401,403, filed Mar. 26, 2003, which are each incorporated by reference.

In practicing aspects of the present invention (e.g., producing protected enzymes, performing reactions, etc), many conventional techniques in molecular biology and recombinant DNA are optionally utilized. These techniques are well known and are explained in, for example, Current Protocols in Molecular Biology, Volumes I, II, and III, 1997 (F. M. Ausubel ed.); Sambrook et al., 2001, Molecular Cloning: A Laboratory Manual, Third Edition, Cold Spring Harbor Laboratory Press, Cold Spring Harbor, N.Y.; Berger and Kimmel, Guide to Molecular Cloning Techniques Methods in Enzymology volume 152 Academic Press, Inc., San Diego, Calif. (Berger), DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); Methods in Enzymology Vol. 154 and Vol. 155 (Wu and Grossman, and Wu, eds., respectively).

Figure 9:
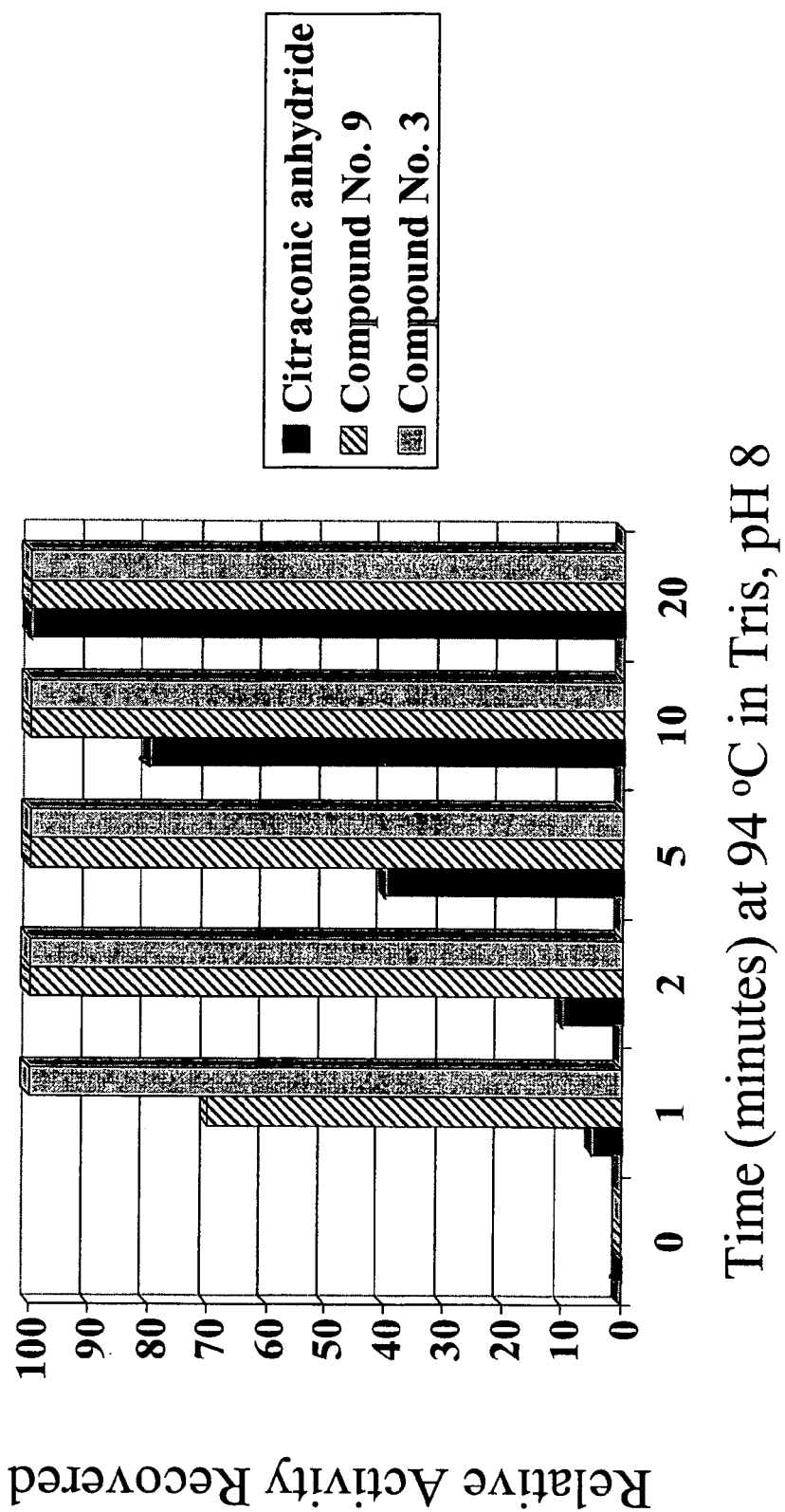
FIG. 9. Relative activity of Taq DNA polymerases protected with different protecting reagents (compound No. 1, compound No. 9 and citraconic anhydride, respectively) following different incubation times.
Figure 10:
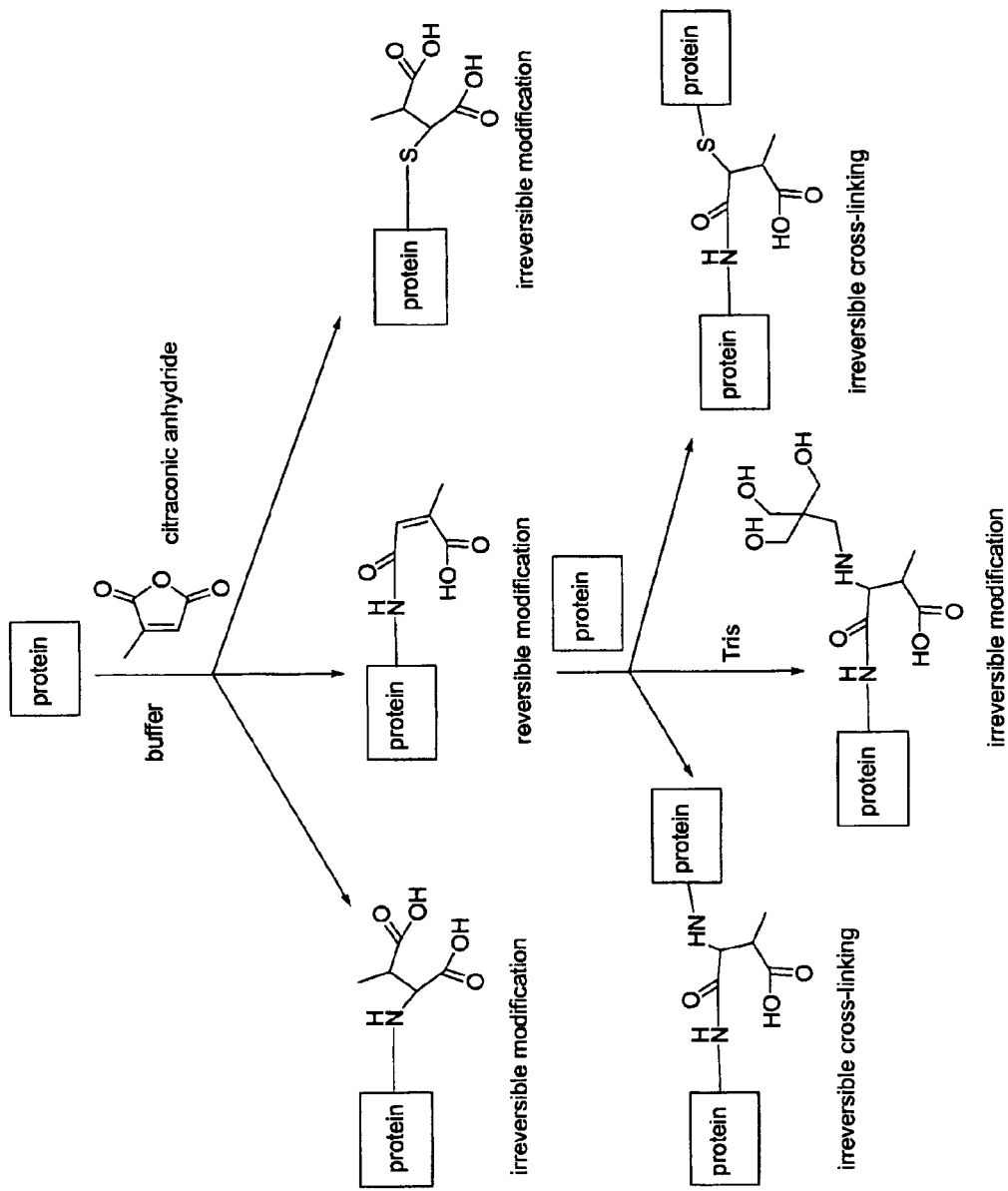
FIG. 10. Scheme showing reversible and irreversible enzyme modifications with citraconic anhydride.

In embodiments where the protected polymerase is Taq polymerase, the protected Taq polymerase of the invention is advantageous over Taq polymerase protected with citraconic anhydride, which is marketed as AmpliTaq Gold (U.S. Pat. No. 5,677,152). One major advantage is that the protected Taq of the present invention can be activated significantly faster than Taq protected with citraconic anhydride (FIG. 9). Another major advantage is that protected Taq according to the present invention is less likely to lose its capacity to be deprotected during storage and handling. This is due to the fact that protecting reagents of the invention appear to be generally more specific in the labeling reaction than citraconic anhydride (a maleic anhydride derivative) or other similar maleic anhydride protecting reagents e.g. disclosed in U.S. Pat. No. 5,677,152. Maleic anhydride or any of its derivatives, thus called a maleic anhydride reagent, generally comprises two reactive sites: the anhydride site and the C=C double bond site, both of which are capable of reacting with an amine. In addition, the C=C site can also react with a thiol. The anhydride site may react with an amine to form a heat-reversible amide linkage while the C=C site may react with an amine or a thiol via Michael addition to form an irreversible C—N or C—S bond. Although the reaction between the anhydride site and an amine is expected to be much faster than the reaction between the C=C site and an amine or thiol, the possibility of side reactions exists, where a small number of the available amino groups of the enzyme react with the C=C site. Formation of any irreversible C—N and/or C—S bond may lead to irreversible damage of enzyme activity, particular if the irreversibly protected amine and/or thiol is functionally important. More importantly, unlike the anhydride site, which either reacts with an amine or hydrolyzes to the unreactive dicarboxylic acid, the C=C double bond does not hydrolyze under labeling and storage conditions, which suggests that Taq protected with maleic anhydride or a maleic anhydride derivative can undergo further side-reactions at the C=C site of the attached protecting groups. Possible side-reactions may include cross-linking of the attached modifying groups with another amine or thiol from either within the same enzyme molecule or from another enzyme molecule, and reaction with Tris buffer. In the first side-reaction, not only the C—N or C—S bond is irreversible as mentioned above, but the amide bond at the other end of the cross-linkage also becomes irreversible or very difficult to cleave. This is due to, in part, that cleavage of the amide bond relies on the conformational constraint of the protecting group whereas the addition of an amine or thiol to the C=C bond diminishes that constraint of the modifying group. In the second possible side-reaction, the amino group of Tris, a commonly used buffering agent for Taq storage and for DNA amplification, may add to the C=C site, thereby converting the rigid C=C double bond to a flexible C—C single bond and consequently making the modifying group irreversibly attached to the amine or at least much more difficult to remove. FIG. 10 schematically illustrates protein modification with citraconic anhydride and the associated side-reactions. Protecting reagents of the invention generally lack a second reactive site prone to nonspecific amine modification and side-reactions found with maleic anhydride or other maleic anhydride derivative protecting reagents. It will be obvious to one skilled in the art that the above advantages for the protected Taq can also be readily extended to other enzymes protected using a protecting reagent of the invention.

In another aspect, the present invention makes it possible to modify different thermostable enzymes with different modifying groups so that each protected enzyme has a different activation temperature. Accordingly, a composition is provided comprising a first population of protected polymerases, wherein the first population is substantially inactive relative to a corresponding first population of unprotected polymerases; a second population of protected polymerases, wherein the second population is substantially inactive relative to a corresponding second population of unprotected polymerases; wherein individual polymerases within said first population of protected polymerases are convertible to corresponding unprotected polymerases under a first set of suitable deprotection conditions, but under which conditions individual polymerases of said second population of protected polymerases are not convertible to corresponding unprotected polymerases; and further wherein individual polymerases within said second population of protected polymerases are convertible to corresponding unprotected polymerases under a second set of suitable deprotection conditions. As described in Example 5, a thermostable enzyme protected with compound No. 9 may be activated at a temperature as low as 60° C. A thermostable enzyme protected with compound No. 9 and another thermostable enzyme protected with citraconic anhydride (or any other protecting reagent, including those disclosed in U.S. Pat. No. 5,677,152 and U.S. Pat. No. 6,183,998) can be activated independently in the same reaction mixture by first incubating in a first set of deprotection conditions at about 60° C. to release the first enzyme and then incubating in a second set of deprotection conditions at about 95° C. to release the second enzyme. Such a reaction mixture may be a reverse transcription PCR reaction as described herein. For example, a reverse transcriptase (RTase) protected with compound No. 9 or another similar protecting reagent of the invention can be combined with Taq DNA polymerase protected with citraconic anhydride for reverse transcription and subsequent DNA amplification in a single tube. The protected RTase is first activated at about 40 to about 60° C., for the reverse-transcription stage while leaving the protected Taq still inactive. Once the reverse transcription is complete, the protected Taq is activated at about 80 to about 100° C., followed by PCR. Because both enzymes require heat-activation, nonspecific product formation due to false priming during reaction set up may be significantly reduced.

Methods of Use

One embodiment of the invention relates to chemically protected enzymes, e.g., thermostable enzymes used in a nucleic acid amplification system. Amplification may be carried out by DNA polymerases such as Taq polymerase, Pfu polymerase, T7 DNA polymerase, Klenow fragment of *E. coli* DNA polymerase, and/or RNA polymerases such as reverse transcriptase, or any of the polymerases mentioned herein.

One possible amplification method is the polymerase chain reaction (PCR). General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 55° C. to 65° C. for 1 to 2 minutes, and (c) extension at 68° C. to 75° C. for at least 1 minute with the final cycle extended to 10 minutes.

Any amplification system that uses a thermostable enzyme can be used with the protected polymerases of the invention. Merely by way of example, the invention may be applied to a thermostable enzyme involved in any of the following systems including, but not limited to, conventional PCR, isothermal amplification, ligase chain reaction, polymerase ligase chain reaction, and repair chain reaction. Deprotection of the protected enzyme can be carried out either as a pre-treatment of the amplification reaction or as an integral part of the amplification reaction. According to one embodiment, the protected enzyme is protected Taq DNA polymerase. Preferably, a sufficient number of the amino groups in Taq are protected so that the protected enzyme is completely or nearly completely inactive at a lower temperature, such as at room temperature, and can be deprotected at a temperature at or above the primer hybridization temperature. For example, Taq may be protected with compound No. 1, or in another embodiment, Taq is protected with compound No. 9.

A protected Taq according to the invention may be useful for PCR by preventing or minimizing nonspecific DNA amplification caused by mis-priming during PCR reaction setup. The protected Taq is typically activated at a temperature above the PCR annealing temperature, for example from about 60° C. to about 70° C., or from about 70° C. to about 80° C., or from 80° C. to about 90° C., or from about 90° C. to about 100° C., for a time sufficient to achieve a desired degree of enzyme activation prior to PCR cycling. The protected Taq is capable of deprotection in a buffer with pH from about 6 to about 11, or about 7 to about 10, or about 8 to about 9. In some embodiments, the protected enzyme is compatible with PCR buffers, which may exhibit a similar pH range.

Variations and alternative amplification methods are also envisioned as suitable for performing the present invention. A variant of the conventional PCR that can be performed is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

Methods of "quantitative" amplification of nucleic acids are well known to those of skill in the art. For example, quantitative PCR (qPCR) can involve simultaneously co-amplifying a known quantity of a control sequence using the same primers. This provides an internal standard that may be used to calibrate the PCR reaction.

The subject protected polymerases can be employed in reverse transcription PCR reaction (RT-PCR). RT-PCR is another variation of the conventional PCR, in which a reverse transcriptase first converts RNA molecules to double stranded cDNA molecules, which are then employed as the template for subsequent amplification in the polymerase chain reaction. The reaction is maintained at a suitable temperature (e.g., 30-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample. One of skill in the art will appreciate that if a quantitative result is desired, caution must be taken to use a method that maintains or controls for the relative copies of the amplified nucleic acids.

Detection of amplification product in an amplification reaction mixture can be carried out using any known methods, which include, but are not limited to, DNA analysis by gel electrophoresis following the amplification reaction, real-time product detection using a DNA-binding dye or a fluorogenic oligonucleotide probe, and DNA melt curve analysis including high resolution DNA melt curve analysis. According to one embodiment of the invention, the reaction mixture comprising an additional DNA-binding dye so that the product is detected in real-time. Examples of suitable DNA-binding dyes include, but are not limited to, EvaGreen® dye and SYBR Green® I dye. An alternative method of real-time product detection is via the inclusion of a fluorogenically labeled oligonucleotide probe in the reaction mixture. During the course of DNA amplification, the probe is cleaved by the 5'-exonuclease activity of the polymerase to release a fluorescence signal in proportion to the amount of product formation. Use of fluorogenic oligonucleotide probes for real-time detection of amplification products has been described previous in numerous patents and academic publications. All of those probes are suitable for the present invention. Merely by way of examples, suitable probes include TaqMan probes, AllGlo probes, Molecular beacons, and MGB probes. DNA melt curve analysis is another useful method for product detection. In this method, a DNA-binding dye is added either to the reaction mixture prior to the amplification reaction, or to the amplification product following the reaction, and the fluorescence change of the product solution as a function of temperature is monitored. Like the gel electrophoresis method, melt curve analysis is useful in determining both the amount and specificity of the product but with more convenience and better sensitivity. A variant of regular melt curve analysis is so-called high resolution melt curve analysis, which permits detection of single mutation. Additional nucleic acid detection methods are, for example, nucleic acid binding agents such as those disclosed in U.S. Pat. No. 6,814,934, probes used in assays such as those described in U.S. Pat. Nos. 5,210,015, 5,487,972, and 6,214,979. In some embodiments, nucleic acid detecting agents are molecules that interact with double stranded nucleic acid. In certain embodiments, fluorescent indicators may be "intercalating fluorescent dyes," which are molecules which exhibit enhanced fluorescence when they intercalate with double stranded nucleic acid. In certain embodiments, "minor groove binding fluorescent dyes" may bind to the minor groove of double stranded DNA. In certain embodiments, fluorescent dyes and other fluorescent molecules can be excited to fluoresce by specific wavelengths of light, and then fluoresce in another wavelength. According to certain embodiments, dyes may include, but are not limited to, acridine orange; ethidium bromide; thiazole orange; pico green; chromomycin A3; SYBR® Green I (see U.S. Pat. No. 5,436,134); quinolinium, 4-[(3-methyl-2(3H)-benzoxazolylidene) methyl]-1-[3-(trimethylammonio) propyl]-, diiodide (YO-PRO®); and quinolinium, 4-[(3-methyl-2(3H)-benzothiazolylidene) methyl]-1-[3-(trimethylammonio) propyl]-, diiodide (TOPRO®). SYBR® Green I, YOPRO®, and TOPRO®) are available from Molecular Probes, Inc., Eugene, Ore. All of the above mentioned product detection methods and their variants are suitable for use with the present method of nucleic acid amplification.

In this and other embodiments, the polymerases of the invention are used to extend a nucleic acid strand through the incorporation of nucleoside phosphates. Such extensions may take place, for example, in a nucleic acid amplification reaction mixture. Nucleoside phosphates suitable for this purpose include nucleosides linked to one or more phosphate groups. Such nucleoside phosphate include, but are not limited to, nucleoside monophosphates, nucleoside diphosphates, nucleoside triphosphates, nucleoside pentaphosphates and others. For example, suitable nucleoside phosphates are disclosed in U.S. Pat. Nos. 7,052,839, 7,041,812, 4,994,373, 5,175,269, and 5,241,060. Nucleoside phosphates may be naturally occurring or may comprise additional modifications such as labels (e.g. fluorescent, chemiluminescent, colorimetric, fluorescent, mass tag etc.) or other 2' or 3' modifications.

Kits

The invention also provides a kit comprising a protected polymerase according to the invention and a nucleic acid detection reagent. The nucleic acid detection reagent may be a fluorescent reagent such as for example EvaGreen or SYBR Green I. A kit may additionally comprises one or more reagents selected from the group consisting of a primer, template, nucleoside phosphate and buffer. A kit may additionally comprise a user instruction manual. Such a user manual may instruct a user to perform a reaction such as a nucleic acid amplification reaction.

Instruments and Other Methods of Use

Also provided herein is an instrument for use in a nucleic acid amplification reaction comprising multiple thermal cycles, comprising: an automated thermal cycler capable of alternately heating and cooling, and adapted to receive, at least one reaction vessel containing an amplification reaction mixture comprising a template nucleic acid, a nucleotide, a nucleic acid detecting agent, and a population of protected polymerases of the invention; wherein the cycler is programmable to control initiation of the amplification reaction by controlling deprotection of the protected polymerases. In some embodiments, the instrument additionally comprises a display capable of indicating the extent of deprotection of the protected polymerases and/or indicate the set of conditions in which one or more populations of deprotected polymerases may become deactivated. Such a display may aid the user of the instrument in performing the reactions disclosed herein.

The instrument may further comprise a detector operable to detect a fluorescence optical signal while the amplification reaction is in progress, which fluorescence optical signal is related to the presence and/or amount of amplified nucleic acid in the reaction vessel. The detector is for example operable to detect a fluorescence optical signal in at least one of the following wavelength regions: from about 510 to about 530 nm, from about 540 to about 550 nm, from 560 to about 580 nm, from about 585 to about 595 nm, from 590 to about 610 nm, from 660 to about 680 nm, from about 690 to about 710 nm, or from 770 to about 790 nm. The instrument may also be adapted to receive a plurality of reaction vessels, each containing an amplification reaction mixture.

Other instruments known in the art are also suitable for performing the methods of the invention. Such instruments are described, for example, in U.S. Pat. Nos. 6,814,934, 5,475,610, 5,928,907, 5,972,716, and 6,015,674, all of which are hereby incorporated by reference.

In some embodiments, the protected enzymes of the invention are used to perform single molecule reactions. Such reactions include, but are not limited to, single molecule sequencing and rolling circle reactions. Methods for performing such reactions are described in U.S. Pat. No. 7,315,019; U.S. Patent Application No. 2003/0044781; M. J. Levene, J. Korlach, S. W. Turner, M. Foquet, H. G. Craighead, W. W. Webb, SCIENCE 299:682-686, January 2003 "Zero-Mode Waveguides for Single-Molecule Analysis at High Concentration". Additional methods are disclosed, for example, in U.S. Pat. Nos. 7,056,676, 7,056,661, 7,052,847 and 7,033,764.

The polymerases of the invention may also be used to perform nucleic acid amplification reaction on solid supports such as arrays. Such techniques are described, for example, in U.S. Pat. Nos. 5,922,591, 6,582,938, 6,485,944, 6,511,803, 6,387,621 and 6,248,521.

EXAMPLES

Example 1

Measurement of Polymerase Activity Assay

Polymerase activity assays were performed by following a published procedure (Nucleic Acids Research, 2004, Vol. 32, No. 3 1197-1207) with minor modifications. Specifically, DNA polymerase to be assayed was added to a pre-incubated 1X AmpliTaq DNA polymerase buffer II (Applied Biosystems, Inc) containing 2.5 mM MgCl$_2$, 0.25 mM each of dNTP and 100 nM primer (sequencing: 5'-CGCCAGGGTTTTC-CCAGTCACGACGTTGTAAAACGACGGCC-3' (SEQ ID NO:1))-annealed ssM13 mp18 DNA at a designated temperature. While the incubation continued, an aliquot (5 µL) was taken at 0, 1, 2, 3, 5, 7, 10, 15, 20, 25, 30, 35, 40, 50 and 60 minute time points, respectively and added to 195 µL solution containing 0.1 M EDTA and 1X EvaGreen (Biotium, Inc., Hayward, Calif.). The amount of DNA synthesized was quantified using a fluorescence plate reader (BioRad) at room temperature. The unit activity of the DNA polymerase was determined by comparing its initial rate with that of AmpliTaq from Applied Biosystems.

Example 2

Modification of Taq DNA Polymerase

Stock solution of compound No. 9 was prepared in anhydrous DMF at 100 mg/mL concentration. Half a milliliter (0.5 mL) of the protecting reagent solution was added to 4.5 mL of Taq at 1.1 mg/mL in 0.1 M pH 9.0 Tris buffer. The resulting solution was incubated at 4° C. overnight.

Example 3

PCR Using Taq Protected with Compound No. 9

Figure 5:
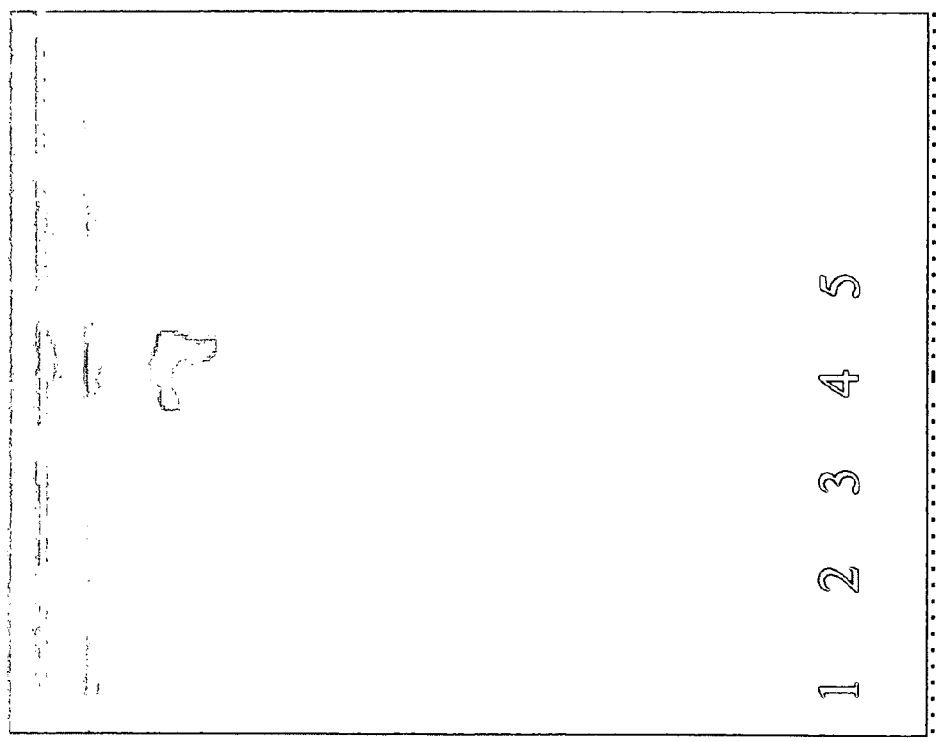
FIG. 5. Comparison of PCR products in agarose gel between using Taq DNA polymerase and using a protected Taq DNA polymerase according to the present invention.
Figure 6:
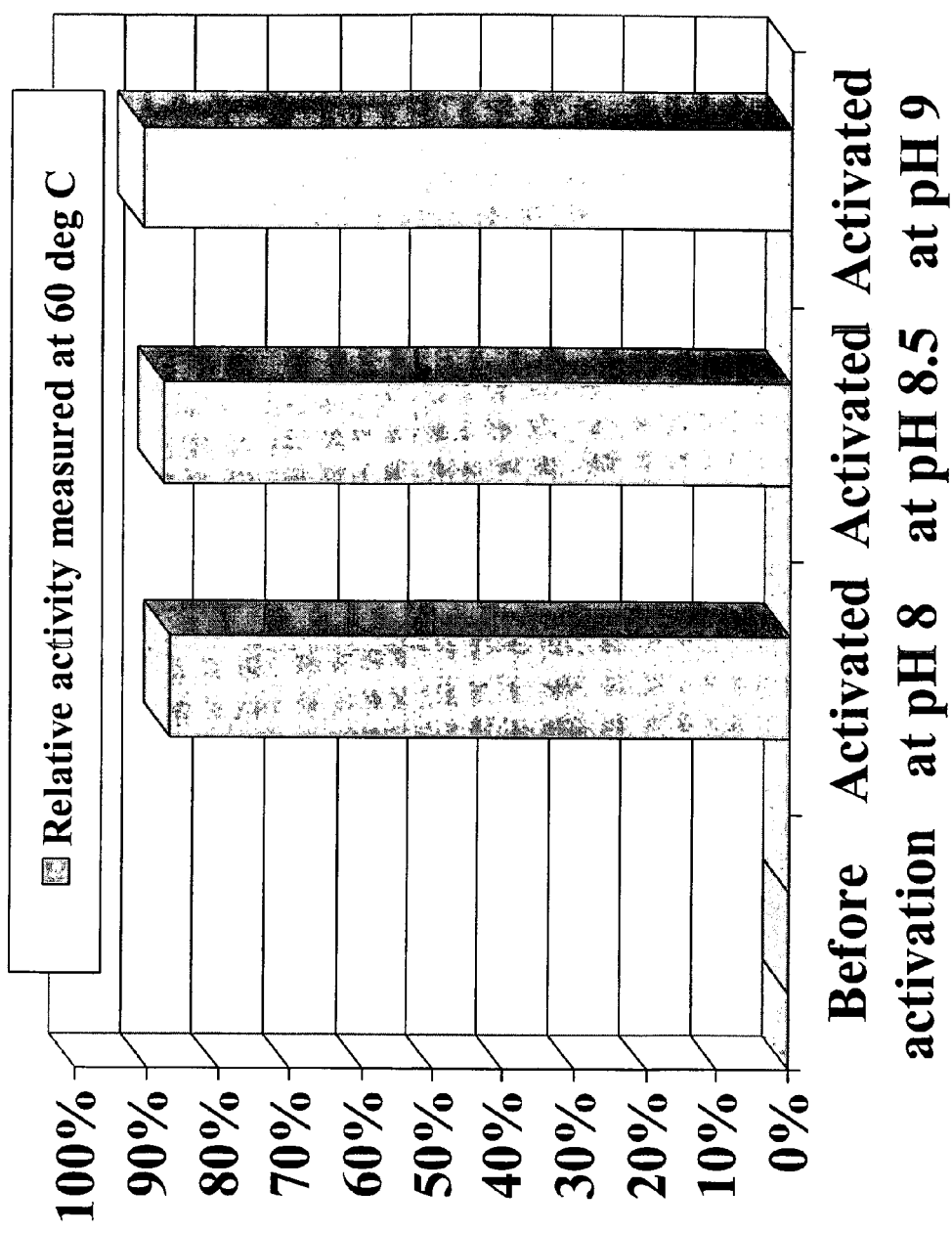
FIG. 6. Relative enzyme activity of Taq protected with compound No. 9 following activation at 94° C. in Tris buffer of pH 8.0, pH 8.5 and pH 9.0, respectively.

To assess the effectiveness of protected DNA polymerases of the invention in reducing nonspecific DNA amplification in PCR, Taq protected with compound No. 9 and unprotected Taq were compared in the amplification of a fragment of human DNA. PCR experiments were performed in 20 µL-sized reaction solutions containing 1X AmpliTaq buffer, 0.25 mM dNTP, 2.5 mM MgCl$_2$, 500 ng each of forward and reverse primers (Forward primer: TGGGAACTGCAACT-CATCTGG (SEQ ID NO:2); Reverse primer: GCGCTC-CTCTCTCCAGCAG (SEQ ID NO:3)), 20 or 0.0 ng human DNA (Applied Biosystems), 2 units of either Taq protected with compound No. 9 or unprotected Taq. PCR's without the target DNA served as nontemplate controls (NTC). PCR protocol involved 2 minutes of heating at 95° C., followed by 40 cycles of 5-second incubation at 95° C. and 60-second incubation at 60° C. At the end of each reaction, PCR product was analyzed on a 4% agarose gel (FIG. 5). PCR using regular Taq produced non-specific products both with target DNA (Lane 4) and with NTC (Lane 5) as indicated by the widely diffused lower molecular weight smears, while PCR using a protected Taq of the invention formed a single band corresponding to the specific amplification product from human DNA (Lane 1) and no apparent product from NTC (Lane 2). Lane 3 is 1 kb DNA ladder (Invitrogen) as reference.

Example 4

Deprotection of Taq Protected with Compound No. 9 at 94° C. and Various pH's

To test for the effect of pH on enzyme activation, the protected Taq DNA polymerase of Example 2 was first reconstituted in 0.1 M Tris of 8.0, 8.5 and 9.0, respectively, at a concentration of 50 nM, and then activated at 94° C. for 2 minutes. Following the activations, enzyme activity assays were performed according to the procedure described in Example 1. As a control, assay was also performed on the unactivated enzyme ("before activation"). The data is summarized in the table below:

|  | Enzyme activation condition | | | |
| --- | --- | --- | --- | --- |
|  | Before activation (control) | Activation at pH 8.0 | Activation at pH 8.5 | Activation at pH 9.0 |
| Relative enzyme activity | 0% | 87% | 88% | 91% |

The result demonstrates that the protected enzyme can be well activated within the pH 8-9 range, which is typically the optimal pH range for the activity of common DNA polymerases. For example, the optimal pH's for Taq and Pfu are 8.3 and 9.0, respectively. This means that enzyme activation and amplification can be conveniently performed in the same buffer.

Example 5

Deprotection of Protected Taq at 60° C.

Taq DNA polymerase protected with compound No. in pH 8.3 Tris was incubated at 60° C., a temperature at which many enzymes derived from mesophiles can survive, to see if enzyme activation could take place at a lower temperature. Relative enzyme activities following different incubation times, as assayed using the method of Example 1, are summarized in the table below:

|  | Incubation time (minutes) at 60° C. | | | |
| --- | --- | --- | --- | --- |
|  | 0.0 | 5.0 | 10.0 | 20.0 |
| Relative Taq activity (assayed at 37° C.) | 0% | 5% | 20% | 80% |

The results demonstrate that significant activation of the protected Taq is achievable at 60° C.

Example 6

Comparison of Activation Kinetics Among Taq DNA Polymerases Protected with Compound No. 1, Compound No. 9 and Citraconic Anhydride, Respectively The three titled protected enzymes (50 nM) were each incubated in pH 8.0 Tris at 94° C. for 0, 1, 2, 5, 10 and 20 minutes, respectively. Enzyme activities following the incubations were assayed at 60° C. according to Example 1. Citraconic anhydride-modified Taq took more than 10 minutes to recover completely while Taq protected with compound No. 1 or compound No. 9 took less than 2 minutes to activate (FIG. 9).

Example 7

Use of Protected Taq DNA Polymerases in Intercalating Dye-Based Real-Time PCR and Effect of the Protected Enzymes on Ct Value To test the protected Taq DNA polymerases for use in real-time PCR and the effect of the protected enzymes on the Ct value, Taq DNA polymerases protected with compound No. 1 and compound No. 9, respectively, and unprotected Taq were each used at a concentration of 2.5, 5, 10 and 25 nM, respectively, in the amplification of a plasmid insert (sequence: CATCCATGACAACTTTGGTATCGTG-GAAGGACTCATGACCACAGTCCATGCCATCAC TGC-CACCCAGAAGACTG (SEQ ID NO:4)). All amplifications were carried out in 20 μL-sized reactions in 1X AmpliTaq Buffer (ABI, Foster City, Calif.) containing 1X EvaGreen dye (Biotium, Hayward, Calif.) 250 μM each of dNTP, 2.5 mM $MgCl_2$, 500 nM each of forward (CATCCATGA-CAACTTTGGTATCGT (SEQ ID NO:5)) and reverse (CAGTCTTCTGGGTGGCAGTGA (SEQ ID NO:6)) primers, $10^5$ copies of the plasmid and the indicated concentration of one of the enzymes. The thermal profile is 40 cycles between 15 second at 95° C. and 60 second at 60° C. after 2 minutes activation at 95° C. The reactions were monitored on BioRad's iCycler iQ. The Ct's of the reactions are tabulated in FIG. 7. Because the Ct values for amplifications using all three enzymes were affected nearly identically as the enzyme concentrations varied, it can be concluded that the two activated enzymes and the unprotected enzyme had similar activity.

Example 8

5'-Exonuclease Activity of the Protected Taq DNA Polymerases

To assess if the 5'-exonuclease activity of the protected enzymes is affected by the modification, Taq DNA polymerases protected with compound No. 1 and compound No. 9, respectively, and unprotected Taq (control) were each tested for use in real-time PCR employing a 5'-exonuclease-cleavable oligonucleotide probe. All PCR experiments were carried out in 20 μL 1X AmpliTaq buffer containing 25 nM any of the enzyme, 250 μM each of dNTP, 2.5 mM $MgCl_2$, 500 nM of forward primer (CCCAAGATAGTTAAGTGG-GATCGA (SEQ ID NO:7)), reverse primer (AATCCAAAT-GCGGCATCTTC (SEQ ID NO:8)) and suitable molar concentration of MAR-labeled AllGlO probe (Sequence: MAR -ATGTAAGCAGCATCATGGAGGTT-MAR (SEQ ID NO:9); AlleLogic Biosciences Co., Hayward, Calif.), $10^7$ copies of a plasmid containing an insert sequence (CCCAAGATAGTTAAGTGGGATCGAGACATGTAA-GCAGCATCATGGAGG TTTGAAGATGCCGCATTTG-GATT (SEQ ID NO:10)).

Figure 8:
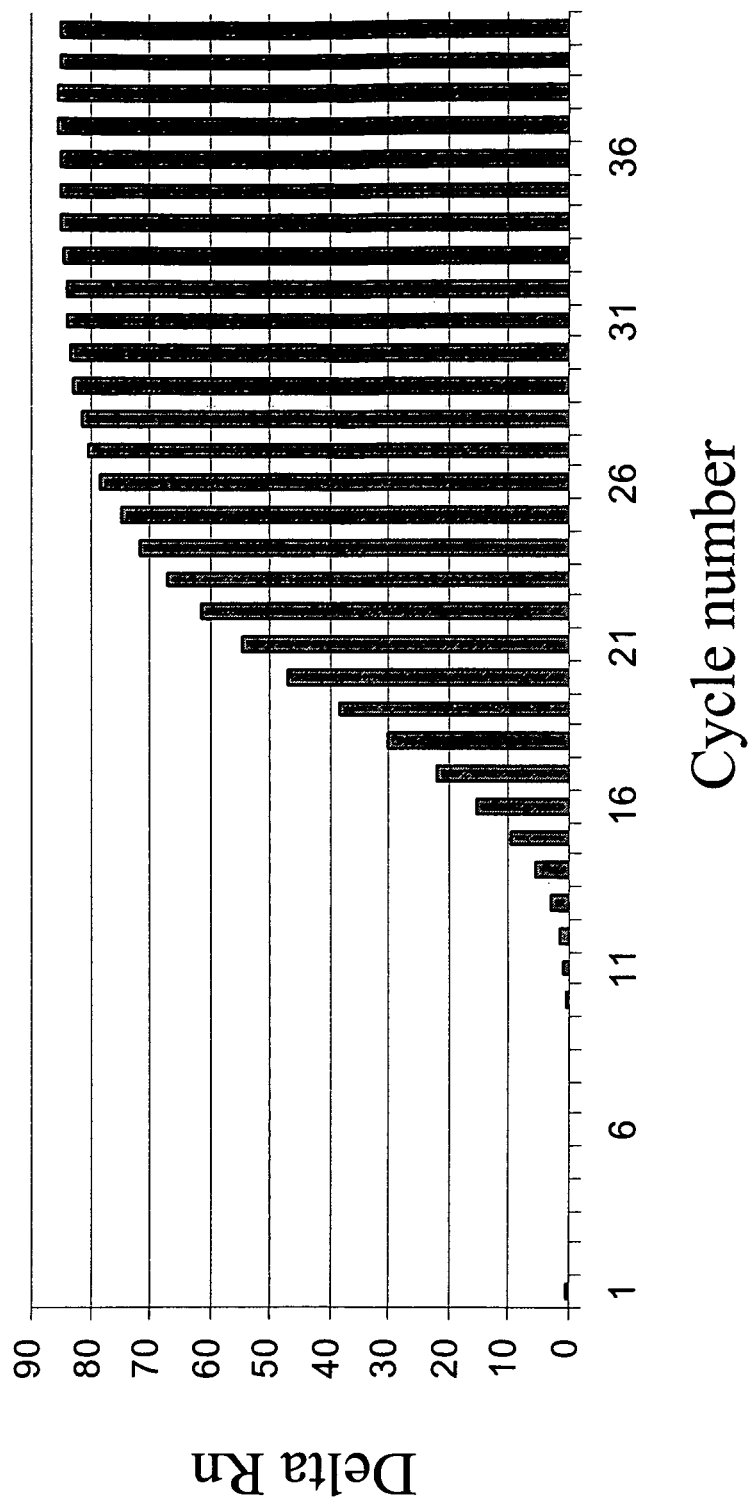
FIG. 8. Amplification curve for PCR using Taq protected with compound No. 9 and a 5'-exonuclease-cleavable AllGlo probe.

The thermo-profile was 92° C. for 2 minutes followed by 40 cycles between 95° C. (15 second) and 50° C. (1 minutes). The reactions were monitored on BioRad's iCycler iQ. The amplification curves for amplifications using all three enzymes are nearly superimposable (FIG. 8, only the curve for reaction using Taq protected with compound No. 9 is shown). The results demonstrate that protected Taq DNA polymerases of the invention retain both polymerase activity and 5'-exonuclease activity.

Example 9

Preparation of Compound No. 1

A mixture of 1,3-cyclohexadiene (840 mg, 10.5 mmol) and citraconic anhydride (1.18 g, 10.5 mmol) was heated at 50° C. in a pressure tube for 24 hrs. After cooling down to room temperature, $Et_2O$ (50 mL) was added and the resulting suspension was stirred at room temperature overnight. The suspension was suction filtered and the filtrate was concentrated in vacuo to give a colorless oil that was purified by column chromatography on silica gel to give compound 2 (310 mg) as colorless solid.

Example 10

Preparation of Compound No. 2

Compound No. 1 (200 mg) was hydrogenated in anhydrous THF using 5% Pd/C as catalyst. The reaction mixture was suction filtered and rotary evaporated to give compound No. 2 as a white solid.

Example 11

Preparation of Compound No. 5

Homophthalic anhydride (15 g) was refluxed in 150 mL methanol in the presence of 10 mL concentrated sulfuric acid for 24 hours. The solution was cooled to room temperature and then concentrated to ~60 mL by rotary evaporation. The solution was partitioned between 200 mL ether and 100 mL ice cold water. The ether layer was separated, washed successively with 150 mL water, 150 mL 10% $NaHCO_3$, 100 mL water and 150 mL saturated NaCl. The ether solution was dried with anhydrous sodium sulfate and then rotary evaporated to give homophthalic acid dimethyl ester. The dimethyl ester (10 g) was dissolved in 100 mL anhydrous THF and the resulting solution was cooled to −15° C. under nitrogen. Two equivalents of lithium bis(trimethylsilyl)amide was introduced, followed by drop wise addition of 2.1 equivalents of methyl iodide. The resulting solution was stirred at 0° C. for 1 hour and then at room temperature overnight. The reaction mixture was quenched by water and then extracted into ether. The ether extract was evaporated and then purified to give a pure product, which was hydrolyzed to the free acid using $NaOH/MeOH/H_2O$, followed by isolation via precipitation in acidic water. The isolated free acid intermediate was converted to the final product compound No. 5 by refluxing in acetic anhydride. Compound No. 5 was purified by silica gel column eluting with EtOAc/hexane.

Example 12

Preparations of Compound Nos. 9 and 10

A solution of furan (6 g, 88.8 mmoles) and 2,5-dihydrothiophene-3,4-dicarboxylic anhydride (11.5 g, 74 mmoles) (Baker, B. R.; Query, M. V.; Kadish, A. F. *J. Org. Chem.* 13, 128 (1948)) in 50 mL $CH_2Cl_2$ was let stand at room temperature under 14 kbar pressure overnight. The major product was isolated by silica gel column eluting with EtOAc/hexane. The product was then hydrogenated in THF using 10% Pd/Pd as catalyst to give compound No. 10 (80%). Compound 10 was desulfurized using H2/Raney nickel to the final product compound No. 9 as a white solid.

Example 13

Amine Modification and De-Modification Using Compound No. 9

To demonstrate that a protecting reagent of the invention can be used for reversibly modifying any amine-containing compound, compound No. 9 (1 mg) was added to a solution of 5-TAMRA-PEO$_3$-amine, trifluoroacetate salt (1 mg) (Biotium Inc, cat #90107) in DMF (100 µL) containing Et$_3$N (5 µL). The mixture was stirred at room temperature for 1 hour. TLC (eluent: CHCl$_3$:MeOH:AcOH=7:3:0.5) showed the disappearance of amino-TAMRA and the formation a higher R$_f$ spot that corresponded to the adduct product. Tris buffer (500 µL, 10 mM TrisHCl at pH=8.2) was added and the mixture was heated at 95° C. for 10 minutes. TLC (eluent: CHCl$_3$:MeOH:AcOH=7:3:0.5) showed the regeneration of the amino-TAMRA compound, thus confirming that compound No. 9 could be used to reversibly modifying an amine compound.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of reversibly protecting a nucleophilic group of a polypeptide comprising:
   a. providing a nucleophilic group;
   b. reacting the nucleophilic group with a reagent of the formula:

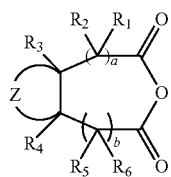

wherein $R_1$, $R_2$, $R_5$ and $R_6$ are hydrocarbon residues, substituted or unsubstituted;
   a and b are independently 0 or 1;
   $R_3$ and $R_4$ are independently —H or a substituent, wherein at least one of $R_3$ and $R_4$ is a substituent when a and b are 0, and wherein $R_3$ and $R_4$ are cis;
   Z forms a 3, 4, 5, 6, 7 or 8-membered ring.

2. The method of claim 1, wherein $R_3$ or $R_4$ is alkyl, wherein the alkyl is optionally methyl.

3. The method of claim 1, wherein the reagent has the formula:

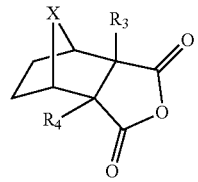

wherein X is O or alkylene, substituted or unsubstituted.

4. The method of claim 1, wherein the nucleophilic group is an ε-amino group of a lysine residue of a polypeptide, wherein the polypeptide is optionally a polymerase.

5. The method of claim 4, wherein the polypeptide is a polymerase selected from Bst DNA polymerase, Taq DNA polymerase, and a reverse transcriptase.

* * * * *

UNITED STATES PATENT AND TRADEMARK OFFICE
CERTIFICATE OF CORRECTION

PATENT NO. : 8,691,968 B2  Page 1 of 1
APPLICATION NO. : 13/001735
DATED : April 8, 2014
INVENTOR(S) : Mao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 378 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgccagggtt ttcccagtca cgacgttgta aaacgacggc c                         41

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgggaactgc aactcatctg g                                               21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgctcctct ctccagcag                                                  19

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
catccatgac aactttggta tcgtggaagg actcatgacc acagtccatg ccatcactgc     60
cacccagaag actg                                                       74
```

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catccatgac aactttggta tcgt                                           24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtcttctg ggtggcagtg a                                              21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccaagatag ttaagtggga tcga                                           24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatccaaatg cggcatcttc                                                20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
atgtaagcag catcatggag gtt                                            23

<210> SEQ ID NO 10
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cccaagatag ttaagtggga tcgagacatg taagcagcat catggaggtt tgaagatgcc    60
gcatttggat t                                                         71
```